United States Patent [19]
Carol

[11] Patent Number: 5,622,187
[45] Date of Patent: Apr. 22, 1997

[54] METHOD AND APPARATUS FOR PATIENT POSITIONING FOR RADIATION THERAPY

[75] Inventor: Mark P. Carol, Sewickley, Pa.

[73] Assignee: Nomos Corporation, Sewickley, Pa.

[21] Appl. No.: 315,929

[22] Filed: Sep. 30, 1994

[51] Int. Cl.⁶ .................................................. A61B 17/00
[52] U.S. Cl. ............................ 128/897; 378/65; 378/205; 250/491.1
[58] Field of Search .................................. 606/130, 897; 128/653.1; 250/491.1, 492.3; 378/65, 205, 206; 600/1–4

[56] References Cited

U.S. PATENT DOCUMENTS

| | | | |
|---|---|---|---|
| 4,896,673 | 1/1990 | Rose et al. | 601/4 X |
| 5,037,374 | 8/1991 | Carol | 600/1 |
| 5,163,430 | 11/1992 | Carol | 128/653.1 |
| 5,197,476 | 3/1993 | Nowacki et al. | 601/4 X |
| 5,207,688 | 5/1993 | Carol | 606/130 |
| 5,315,630 | 5/1994 | Sturm et al. | 378/65 |
| 5,446,548 | 8/1995 | Gerig et al. | 128/653.1 X |

FOREIGN PATENT DOCUMENTS 0246611  10/1988  Japan ............................. 356/375

OTHER PUBLICATIONS

"Compute-RX-Comp" Ad; Medicalibration Physics Consultation Service.
"The Ottawa System for Fractionated Stereotactic Radiotherapy" Szanto; Reprint of Poster (6 pages) Presented at 1994 AAPM Meeting.
"Radiotherapy –Par Scientific A/S" Ad; 3 pages.
"Autocomp", Nuclear Associates, 2 pages.

Primary Examiner—Ruth S. Smith
Attorney, Agent, or Firm—Ben D. Tobor

[57] ABSTRACT

A method and apparatus for positioning a patient upon a treatment table of a linear accelerator includes a camera secured to the gantry of the linear accelerator and a plurality of light emitting diodes mounted with respect to the patient which are viewed by the camera.

25 Claims, 3 Drawing Sheets

METHOD AND APPARATUS FOR PATIENT POSITIONING FOR RADIATION THERAPY

FIELD OF THE INVENTION

The invention relates to a method and apparatus for use in positioning a patient upon a treatment table of a linear accelerator for providing radiation therapy treatment of a lesion within a patient's body through the use of a camera and a plurality of light emitting diodes which are viewed by the camera.

DESCRIPTION OF THE PRIOR ART

Radiation therapy can be effective in treating certain types of cancers if a sufficient radiation dose is delivered to the tumor, or lesion, volume; however, complications may result from use of the necessary effective radiation dose, due to damage to healthy tissue which surrounds the tumor, or lesion, or to other healthy body organs located close to the tumor. The goal of conformal radiation therapy treatment is to confine the delivered radiation dose to only the tumor volume defined by the outer surfaces of the tumor, while minimizing the dose of radiation to surrounding healthy tissue or adjacent healthy organs. If the effective radiation dose is not delivered to the proper location within the patient, serious complications may result, whereby in the delivery of conformal radiation therapy treatments, as well as in static radiation therapy treatments, the position of the patient upon the treatment table is very important. The patient usually has a radiation therapy treatment plan prepared, based upon a diagnostic study through the use of computerized tomographic ("CT") scanning, magnetic resonance ("MR") imaging, or conventional simulation films, which are plain x-rays generated with the patient in the position which will be used by the patient during the radiation therapy treatment. Regardless of which technique, CT scanning, MR imaging, or simulation films, is used at the time of the diagnostic study to develop the radiation therapy treatment plan, it is necessary to relate the patient's position at the time of the diagnostic study to how the patient will be positioned at the time of the radiation therapy treatment. If this relationship of the patient's position is not correct, the radiation dose may not be delivered to the correct location within the patient's body.

Traditional techniques used in the positioning of patients during radiation therapy treatments include: laser lights with tattoos or other markers; non-invasive immobilization devices; and invasive immobilization devices. When tattoos, or markers, are utilized to position the patient during the radiation therapy treatment, the tattoos are placed on the patient's body, while they are on the diagnostic table, in locations corresponding to the tumor, or lesion, volume. These tattoos are aligned to wall-mounted laser lights which cross at the isocenter of gantry rotation of the linear accelerator which is typically used to provide the radiation therapy treatment. The isocenter of gantry rotation is the point where the radiation beams from the linear accelerator intersect as the gantry of the linear accelerator carrying the radiation beam source rotates around the patient. The position of the patient is adjusted until the tattoos are aligned with the laser lights. The treatment table of the linear accelerator, or other radiation device, is locked in place, and the patient is immobilized and the radiation therapy treatment is started.

Non-invasive immobilization involves making a mold of the patient on which tattoos, or other markers, are placed when the patient is properly positioned upon the diagnostic table. At the time of the radiation therapy treatment, the same mold is placed upon the treatment table, and the patient is placed in the mold, after which the radiation therapy treatment begins. One type of non-invasive immobilization device is disclosed in U.S. Pat. No. 5,207,688, entitled "Non-Invasive Head Fixation Method and Apparatus", assigned to the assignee of the present application, and this patent is incorporated herein by reference. The device of U.S. Pat. No. 5,207,688, can be used during CT scanning or MR imaging. A radiopaque marker on the surface of the immobilization device can be identified in the CT scanner or MR imager. The coordinates of the marker and the tumor, or lesion, can be generated in reference to the coordinate system of the CT or MR device. The coordinate offsets of the tumor, or lesion, with respect to the marker can then be generated. When the patient is positioned on the treatment table of the linear accelerator, or other radiation therapy treatment device, the wall-mounted laser lights in the treatment room are first aligned with the external marker. The treatment table may then be adjusted using the tumor, or lesion, coordinate offsets, so that the tumor, or lesion, is brought to the isocenter of gantry rotation of the linear accelerator. The patient then can be treated.

Invasive immobilization employees the same techniques as non-invasive immobilization, except that the immobilization device is secured to the patient in an invasive fashion with screws, pins, or other similar device. The invasive immobilization device stays upon the patient for the duration of the patient's treatment. An example of one such invasive immobilization device is that of U.S. Pat. No. 5,163,430, entitled "Method and Apparatus for Performing Stereotactic Surgery", commonly assigned with the present application, and this patent is incorporated herein by reference.

Electronic systems have also been developed to check proper initial patient positioning and to assess whether or not the patient moves during the radiation therapy treatment. An example of one such system is the "Ottawa system for Fractionated Stereotactic Radiotherapy". This system includes a patient position monitoring system consisting of two charged coupled device cameras mounted to the ceiling of the treatment room, a diode laser, and a plurality of retroreflective targets secured to the patient. The laser illuminates the retroreflector targets which are then viewed by the cameras. Through the process of triangulation, the position of the retroreflectors at any point in time can be determined by the camera system. Another camera system, known as the Pixys, has been used for triangulating patient position in the operating room suite and in the radiation therapy treatment room. This system uses three unidirectional slit cameras which are used to determine the position of light emitting diodes attached to the patient.

There are certain disadvantages inherent in all of the foregoing patient positioning techniques. A major problem associated with the use of tattoos, non-invasive and/or invasive immobilization devices, is that verification of the position of the patient is dependent upon visually aligning the laser lights with some marker placed either on the patient or on the immobilization device attached to the patient. Additionally, the markers, such as tattoos or screws, may be disfiguring to the patient, or it may be difficult to align the laser lights with such markers. Correct alignment may also be subject to the technologist's interpretation of the coincidence of the laser lights with the patient markers. Another disadvantage with these techniques is that there is no means to indicate whether or not the patient has moved after the radiation therapy treatment has begun. Normally, the patient is positioned upon the treatment table, and the treatment table is locked in place. The technologist leaves the radiation therapy treatment, at which time the radiation therapy treatment is begun. The technologist watches the radiation therapy treatment via videocameras mounted inside the radiation therapy treatment room, which are aimed at the treatment table. Even if close attention is paid throughout the radiation therapy treatment, it is many times difficult for the technologist to be, either quantitatively or qualitatively, aware of small amounts of patient movement, which could affect the desired radiation dose being supplied to the desired tumor, or lesion, volume.

The previously described electronic systems have certain disadvantages associated with them. In order to function properly, the cameras have to be rigidly secured to the ceiling of the radiation therapy treatment room, which many times may be difficult and is a function of the construction of the radiation therapy treatment room. Additionally, the plurality of cameras must be situated in such a manner that each camera can simultaneously see the retroreflective targets or light emitting diodes which are used. If each camera cannot simultaneously see the retroreflective targets or light emitting diodes, the necessary triangulation cannot occur. Additionally, because the cameras are mounted to the ceiling of the radiation therapy treatment room, which in many instances may be low, it may be difficult for cameras to adequately view all regions of interest. A further disadvantage associated with such electronic systems is their cost resulting from the necessity of utilizing multiple cameras, as well as, in one instance, a diode laser.

Accordingly, prior to the development of the present method and apparatus for patient positioning for radiation therapy, there has been no method and apparatus for patient positioning which: does not require the use of disfiguring tattoos, screws, or similar markers; is easy to align, may be used to determine undesired patient movement after the radiation therapy treatment has begun; does not require the use of two cameras secured to the ceiling of the radiation therapy treatment room; and is relatively inexpensive. Therefore, the art has sought a method and apparatus for patient positioning for radiation therapy treatments which: does not require disfiguring tattoos, screws, or other markers; is easy to align; permits continuous monitoring of the position of the patient during the radiation therapy treatment; does not require multiple cameras; does not require a diode laser; and is relatively inexpensive.

SUMMARY OF THE INVENTION

In accordance with the invention, the foregoing advantages have been achieved through the present method and apparatus for patient positioning for radiation therapy. The apparatus for use in positioning a patient upon a treatment table of a linear accelerator for providing radiation therapy treatment, the linear accelerator having a rotatable gantry, and the treatment table having associated therewith a means for immobilizing a portion of the patient with respect to the treatment table, in accordance with one aspect of the present invention, includes: a plurality of light emitting diodes, including means for mounting the plurality of light emitting diodes with respect to the patient; at least one camera for viewing the plurality of light emitting diodes; and means for mounting the at least one camera to the gantry of the linear accelerator, whereby as the gantry rotates, the at least one camera rotates with the gantry and views the plurality of light emitting diodes from at least two different angular positions of the gantry with respect to the treatment table.

A feature of this aspect of the present invention is that the at least one camera may be a single camera, and the at least one camera may be a charged coupled device camera. Another feature of this aspect of the present invention is that the means for mounting the plurality of light emitting diodes may include a means for mounting at least one emitting diode in an external auditory canal of an ear of the patient. A further feature of this aspect of the present invention is that the means for mounting at least one light emitting diode in an ear of the patient may include a quantity of a rapidly setting material, which is adapted to be disposed within, and conformed to, the external auditory canal, and the light emitting diode may be disposed within the rapidly setting material. An additional feature of this aspect of the present invention is that the means for mounting the plurality of light emitting diodes may include a means for mounting at least one light emitting diode to the means for immobilizing a portion of the patient. The means for mounting the plurality of light emitting diodes may also include a means for mounting at least one light emitting diode to the body of the patient.

The method for positioning a patient upon a treatment table of a linear accelerator for providing radiation therapy treatment of a lesion within the patient's body, the linear accelerator having a rotatable gantry, in accordance with another aspect of the present invention, may include the steps of: providing at least one camera mounted to the gantry of the linear accelerator; immobilizing a portion of the patient with respect to the treatment table with a means for immobilizing associated with the treatment table; mounting a plurality of light emitting diodes with respect to the patient; disposing the gantry, with the at least one camera mounted thereto, in a first predetermined position with respect to the patient and generating a first image of the plurality of light emitting diodes with the at least one camera; rotating the gantry, with the at least one camera mounted thereto, to a second predetermined position with respect to the patient, and generating a second image of the plurality of the light emitting diodes with the at least one camera; determining, from the first and second images, the location of the light emitting diodes with respect to the treatment table; and comparing the location of the light emitting diodes, with respect to the treatment table, to a previously determined desired location of the light emitting diodes with respect to the treatment table, whereby if the location of the light emitting diodes with respect to the treatment table indicates the patient is not properly positioned, the patient may be moved whereby the light emitting diodes will be disposed in the desired position.

A feature of this aspect of the present invention may include the step of providing a single camera mounted to the gantry of the linear accelerator. An additional feature of this aspect of the present invention may include the step of mounting at least one of the light emitting diodes with respect to the patient by mounting at least one light emitting diode upon the patient. A further feature of this aspect of the present invention may include the step of utilizing as the at least one camera, a charged coupled device camera, and only one camera may be utilized.

Another feature of this aspect of the present invention may include the step of calibrating the at least one camera with respect to the treatment table before immobilizing at least a portion of the patient with respect to the treatment table. A calibration fixture may be used to calibrate the at least one camera and the calibration fixture may be provided with a plurality of light emitting diodes disposed in a known spatial relationship with each other. Another feature of this aspect of the present invention may include the step of continuously monitoring the locations of the plurality of light emitting diodes during the rotation of the gantry while a radiation therapy treatment is provided to the patient and the step of indicating an undesired location of at least one of the plurality of light emitting diodes during the radiation therapy treatment.

The method and apparatus for patient positioning for radiation therapy of the present invention, when compared with previously proposed prior art methods and apparatus, have the advantages of being: relatively inexpensive; not requiring the use of disfiguring markers, such as tattoos or screws; is easy to align; able to be utilized continuously during the radiation therapy treatment; not dependent upon the use of multiple cameras or a diode laser; and readily utilized in existing radiation therapy treatment rooms without mounting any equipment to the ceiling of the radiation therapy treatment room.

While the invention will be described in connection with the preferred embodiment, it will be understood that it is not intended to limit the invention to that embodiment. On the contrary, it is intended to cover all alternatives, modifications, and equivalents as may be included within the spirit and scope of the invention as defined by the appended claims.

DETAILED DESCRIPTION OF THE INVENTION

Figure 1:
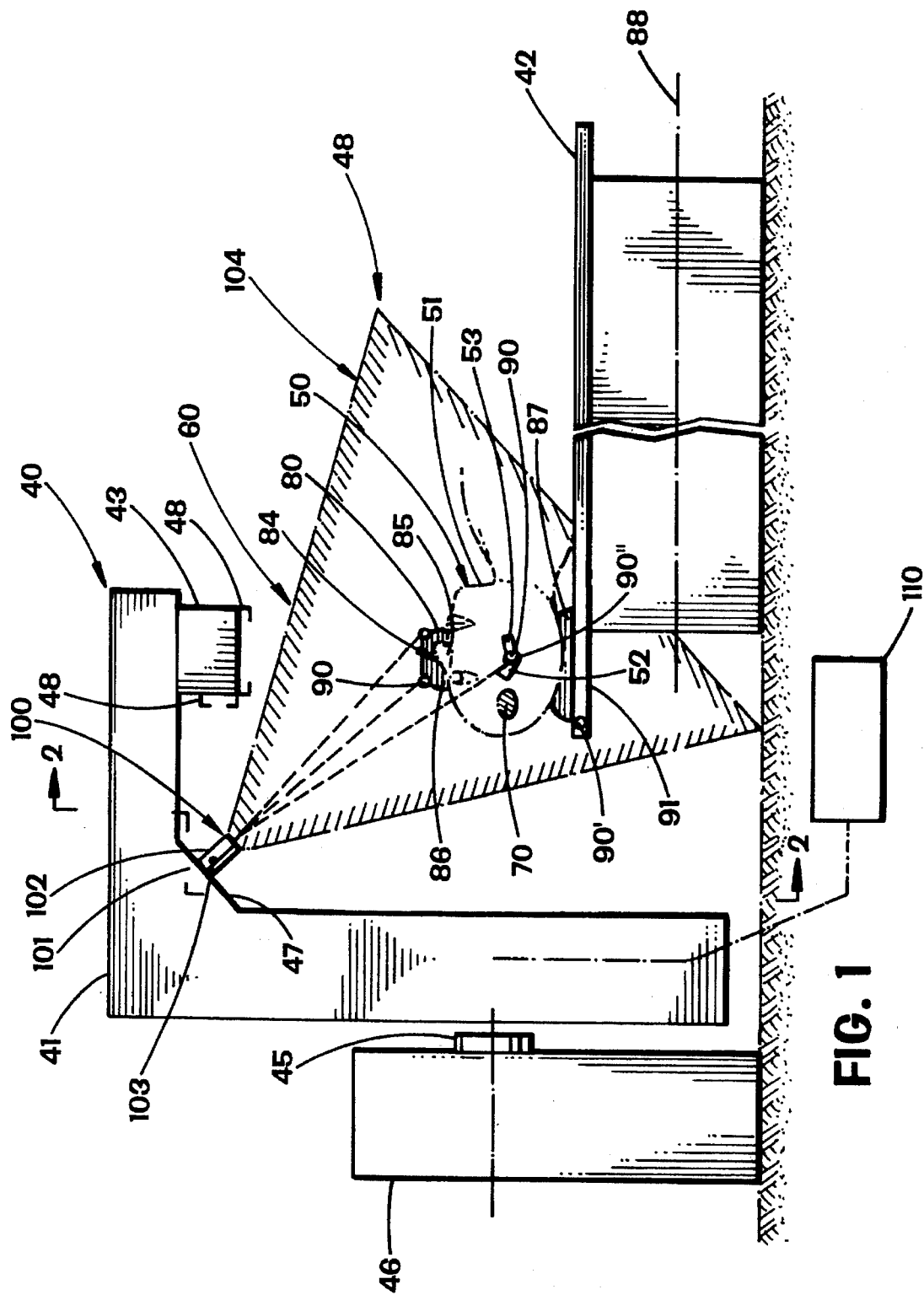
FIG. 1 is a side view of a linear accelerator and apparatus for use in positioning a patient upon a treatment table of the linear accelerator in accordance with the present invention.
Figure 2:
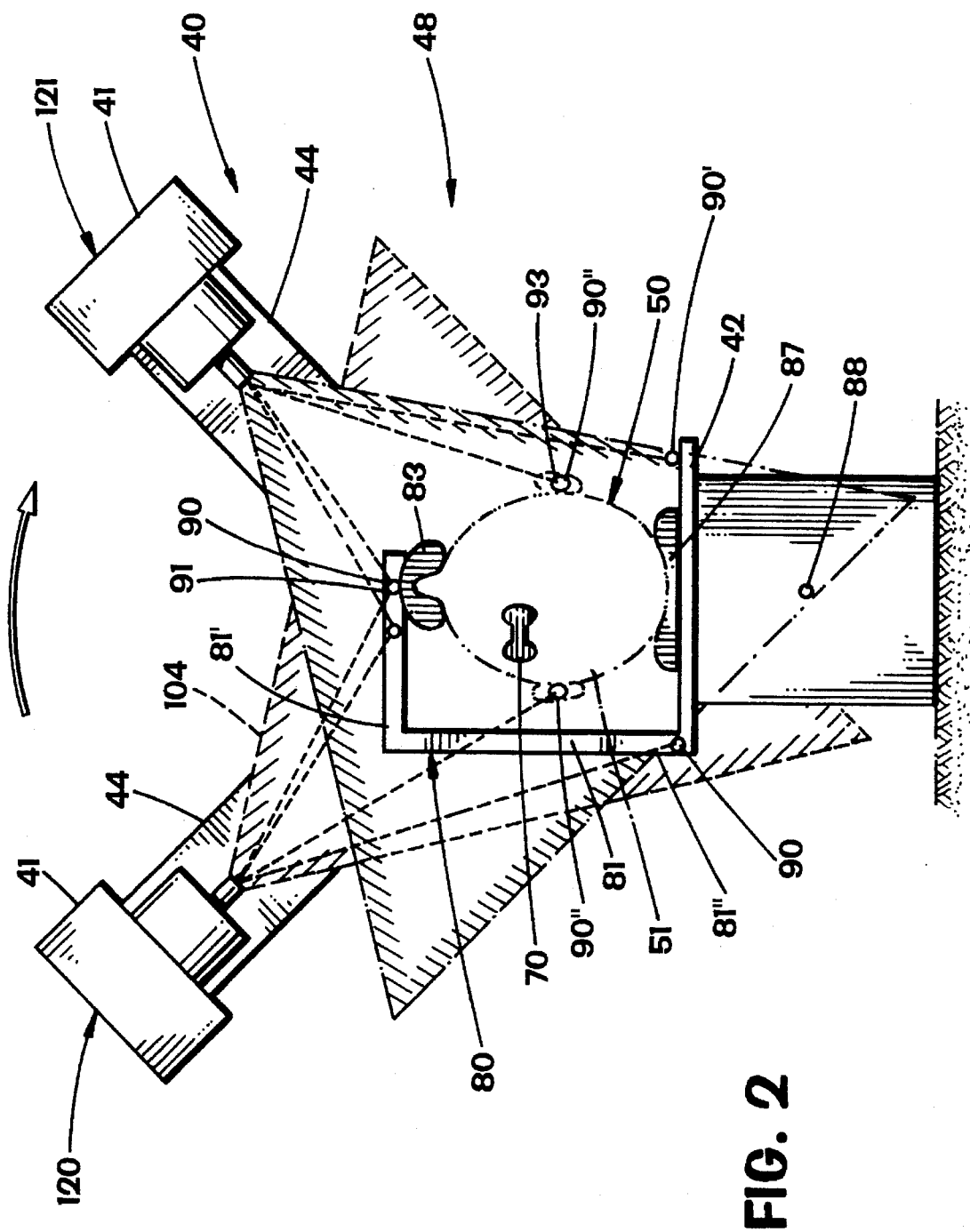
FIG. 2 is a view of the apparatus of FIG. 1 taken along line 2—2 of FIG. 1, the gantry of the linear accelerator being illustrated in two different angular positions with respect to the treatment table after the gantry has been rotated.

With reference to FIGS. 1 and 2, the method and apparatus of the present invention for positioning a patient for radiation therapy treatment will be described. In FIGS. 1 and 2, a linear accelerator 40 is shown as including a gantry 41 treatment table 42, which is typically mounted upon a turntable (not shown), which causes treatment table 42 to rotate therewith, and a conventional collimator, or means for focusing a beam of radiation, 43 for the radiation therapy treatment. Gantry 41 is rotatable about rotatable shaft 45 associated with gantry base member 46, as is known to those of ordinary skill in the field of radiation therapy treatment. Patient 50 is disposed upon treatment table 42, with patient 50 lying upon his or her back, only the head 51 of patient 50 being illustrated for purposes of illustration.

Still with reference to FIGS. 1 and 2, the method and apparatus 60 of the present invention for use in positioning a patient upon treatment table 42 of linear accelerator 40 for providing radiation therapy treatment of a lesion, or tumor, 70 within the body of patient 50 will be described in connection with method and apparatus 60 being clinically used for an intracranial application, wherein the tumor, or lesion 70 is disposed within the head 51 of patient 50, as shown in FIGS. 1 and 2. A portion of patient 50, or the head 51 of patient 50, is immobilized with respect to treatment table 42 by use of a means for immobilizing 80 a portion of patient 50, such the patient's head 51. As illustrated in FIGS. 1 and 2, immobilizing means 80 may be a non-invasive head fixation apparatus, such as illustrated and described in U.S. Pat. No. 5,207,688, which includes a frame 81 secured to treatment table 42, with frame 81 supporting a deformable housing 83 which is adapted to overlie and contact the patient's nasion 84, or the bridge of the patient's nose where it joins the patient's forehead 86. Immobilizing means 80 may also include another deformable housing 87 which restrains rotational movement of the patient's head 51. Through the use of immobilizing means 80, the patient's head 51 is immobilized with respect to treatment table 42. Alternatively, an invasive means for immobilizing could also be used for immobilizing patient's head 51 with respect to treatment table 42, such as the apparatus described in U.S. Pat. No. 5,163,430. While the use of the immobilizing means 80 of U.S Pat. Nos. 5,207,688 and 5,163,430, are preferred, it should be readily apparent to one of ordinary skill in the art that other immobilizing means may be used in connection with the method and apparatus 60 of the present invention.

Prior to patient 50 being disposed upon treatment table 42 of linear accelerator 40, which is typically disposed in a radiation therapy treatment room 48, a radiation treatment therapy plan would have been generated during a CT scanning or MR imaging diagnostic study, at which time the patient 50 would have been immobilized with respect to the diagnostic table utilized in the CT scanning or MR imaging diagnostic study. As will be hereinafter described, the means for immobilizing the patient during the diagnostic study must be the same immobilizing means 80 used in connection with treatment table 42 of linear accelerator 40.

As illustrated in FIGS. 1 and 2, apparatus 60 of the present invention further includes a plurality of light emitting diodes 90 which are mounted with respect to the patient 50 and each light emitting diode 90 includes a means for mounting 91 the plurality of light emitting diodes 90 with respect to the patient 50. Apparatus 60 further includes at least one camera 100 for viewing the plurality of light emitting diodes 90, and a means for mounting 101 the at least one camera 100 to the gantry 41 of the linear accelerator 40. Preferably, the at least one camera 100 is a commercially available charged coupled device camera 102, which includes an angle sensor 103 associated therewith. A suitable power source, or power sources, (not shown) are provided to provide electric current for camera 102 and the plurality of light emitting diodes 90. A small wire (not shown) would be associated with each light emitting diode and connected to the power source in a conventional manner. A suitable computer 110 is operatively associated with camera 102 to process the information and images obtained from camera 102 as will be hereinafter described in greater detail. Preferably, the at least one camera 100 is a single charged coupled device camera 102. However, if desired, more than one camera 102 could be utilized, although an additional camera is not necessary for the practice of the method of the present invention. The second camera would also be mounted upon gantry 41 in a known fixed, spatial relationship with respect to the other camera, or cameras. What is important for the practice of the method of the present invention is that the at least one camera 100 be mounted to the linear accelerator 40, and preferably to the gantry 41.

As shown in FIG. 1, the at least one camera 100 is fixedly secured directly to gantry 41 at an underside surface 47 of gantry 41, whereby the at least one camera 100 has a field of view 104 of the portion, or head 51, of the patient 50 which is being treated by the radiation therapy treatment from linear accelerator 40. Mounting means 101 for camera 102, rigidly secures the camera 102 to the underside surface 47 of gantry 41 as by a plurality of bolts, screws, mounting plate, or similar type of fastening means. Alternatively, the at least one camera 100 could be mounted to the gantry by providing a mounting plate (not shown) which is locked into conventional tray slots 48 associated with the collimator 43 or gantry 41 of linear accelerator 40. Such tray slots 48 are typically provided on linear accelerators for accessories, and are known to those of ordinary skill in the linear accelerator art. Preferably, camera 102 is semi-permanently mounted to gantry 41 as illustrated in FIG. 1, whereby apparatus 60 may not require to be frequently calibrated, as will be hereinafter described in greater detail.

At least some of the light emitting diodes 90 must be mounted to the immobilizing means 80, and preferably a minimum of three light emitting diodes 90 are applied in a non-linear relationship to the immobilizing means 80 in a non-coplanar, non-linear relationship as illustrated in FIG. 2, wherein two light emitting diodes 90 are disposed upon the horizontal portion 81' of frame 81 in a spaced relationship from each other, and a third light emitting diode 90 is disposed toward the bottom of the vertical portion 81" of frame 81. It should be noted that the light emitting diodes 90 mounted to immobilizing means 80 must be disposed in the same location upon immobilizing means 80 when the patient 50 undergoes the MR imaging or CT scanning diagnostic study. The mounting means 91 for the light emitting diodes 90 mounted with respect to patient 50 on immobilizing means 80 may be any suitable fastener, such as glue, epoxy, screws, or bolts, or similar type of fastening devices, whereby the light emitting diodes 90 associated with immobilizing means 80 are fixedly secured to the immobilizing means 80. Some of the plurality of light emitting diodes 90, such as light emitting diode 90' may be also mounted to treatment table 42 by use of the same mounting means 91 previously described.

Still with reference to FIGS. 1 and 2, preferably at least one light emitting diode 90" is mounted in an external auditory canal 52 of patient 50. The mounting means 91 for light emitting diode 90" may be a quantity of a rapidly setting material, such as a dental wax molding material, a thermoplastic material, or similar material, capable of setting and curing at room temperature and being compatible with the human body. The quantity of rapidly setting material 93 is formed into a small ball and molded into the patient's external auditory canal 52 of ear 53. As the rapidly setting material 93 begins to set, light emitting diode 90" is inserted into the material 93 so that light emitting diode 90" sets in place with the material 93, resulting in a custom molded piece including light emitting diode 90'. Preferably, this procedure is followed for both ears 53, and a light emitting diode 90" is mounted within both external auditory canals 52 of ears 53. Alternatively, at least one light emitting diode 90 may be mounted to a portion of the patient, such as head 51 of patient 50, or some other portion of the patient's body. If a light emitting diode 90' is mounted to the body of the patient, the mounting means 91 for such light emitting diode 90 could be a non-disfiguring mounting means 91, such as: surgical skin adhesive used for ostomy bags; other types of suitable adhesive which are compatible with the human body; hook and eye material, such as Velcro®, wherein one layer of the hook and eye material is affixed to the body and the complimentary layer of hook and eye material is secured to the underside of the light emitting diode 90; or other similar types of mounting means 91.

As previously described, prior to the patient receiving a radiation therapy treatment with linear accelerator 40, a diagnostic study is conducted with CT scanning, MR imaging, or simulation films. With the information obtained from the diagnostic study, a radiation treatment plan may be generated in a conventional manner. Such radiation treatment plan can include a conformal radiation treatment plan, as are known in the art. One such conformal radiation therapy treatment plan can be generated in accordance with the PEACOCK™ Conformal Radiation Therapy Planning System which is presently available for use from NOMOS Corporation, of Sewickley, Penna., the assignee of the present application. During the diagnostic study, the patient 50 is immobilized with respect to the diagnostic imaging table of the CT or MR equipment. As previously described, the immobilizing means used during the diagnostic study must be the same as the immobilizing means 80 previously described in connection with FIGS. 1 and 2, and preferably includes at least three light emitting diodes 90 mounted to the immobilizing means 80 and may also preferably include light emitting diodes 90" previously described. The diagnostic study is conducted in a conventional manner and the diagnostic study will determine the spatial coordinates of each of the light emitting diodes with respect to the immobilizing means 80 and the patient 50 by the use of either conventional internal imager software or through use of a computer-based treatment planning system, such as that of the foregoing patent applications. After the desired tumor treatment volume has been defined by the user of the treatment planning system, the treatment planning system determines the proper location for the patient 50 for the radiation therapy treatment, based upon the known spatial coordinates of the plurality of light emitting diodes 90, 90". A three dimensional offset (x, y, z) is generated by the planning system relative to the known location of the light emitting diodes, whereby the lesion, or tumor, 70 may be positioned at the isocenter of the linear accelerator 40 in a known manner.

The patient 50 is then disposed upon treatment table 42 of linear accelerator 40 as previously described in connection with FIGS. 1 and 2. The plurality of light emitting diodes 90, 90', 90" are disposed with respect to patient 50 in the manner previously described, and small wires (not shown) are connected to each of the plurality of light emitting diodes 90, 90', 90" to provide the necessary power for the light emitting diodes. The patient 50 is then positioned upon treatment table 42 so that the conventional wall-mounted laser lights (not shown) included with linear accelerator 40 intersect at light emitting diodes which have been selected by the treatment planning system in a conventional manner. Preferably, the light emitting diodes which would be aligned with the laser lights (not shown) would be the at least three non-coplanar light emitting diodes 90 mounted to the immobilizing means 80. The treatment table 42 may then be positioned in a conventional manner by moving treatment table 42 the proper distance in the x, y and z directions, whereby the lesion, or tumor, 70 is disposed at the isocenter of linear accelerator 40.

With reference to FIG. 2, the gantry 41 is disposed in a first predetermined position with respect to patient 50 as shown at location 120 in FIG. 2. An image of the plurality of light emitting diodes 90, 90', and 90" is generated by camera 102. This image is digitized by a conventional frame grabber, and the digital information is fed into, and stored in, computer 110. The angular disposition of gantry 41 is known from the angle sensor 103 disposed within camera 102, which angle information is also fed into, and stored in, computer 110. Gantry 41 is then rotated to a second predetermined position with respect to patient 50 as indicated at 121 in FIG. 2. Position 121, is likewise known and determined by the angle sensor 103 of camera 102. While gantry 41 is disposed in the second predetermined position 121, a second image of the light emitting diodes 90, 90', and 90" is generated by camera 102, which image is also processed and stored in computer 110. A conventional triangulation algorithm is applied by computer 100, and the location of the light emitting diodes, 90, 90', and 90", with respect to the treatment table 42 is determined. A suitable, known three dimensional reconstruction algorithm, or triangulation algorithm, that may be used computer 110 is that found in *Mathematical Elements for Computer Graphics*, Second Edition, David F. Rogers and J. Alan Adams, McGraw-Hill, Inc. It should be noted that the first and second predetermined positions 120, 121 of gantry 41 illustrated in FIG. 2 have been selected for illustrative purposes only. Preferably, the angle between the first and second predetermined positions 120, 121 should be as close as possible to 90 degrees since as the angle between positions 120, 121 either increases or decreases from 90 degrees, the sensitivity of apparatus 60 may be affected.

The computer 110 has stored therein the locations, or three dimensional coordinates, of the light emitting diodes 90, 90" from the prior identification of their locations from the diagnostic study, and the treatment planning system or imager software has also determined where the tumor, or lesion, 70 is with respect to the light emitting diodes 90, 90". The computer 110 may then compare the location of the light emitting diodes, 90, 90", with respect to the treatment table 42 to the previously determined desired locations of the light emitting diodes 90, 90' with respect to treatment table 42, to determine if the light emitting diodes 90, 90" are disposed at their desired locations with respect to the treatment table 42, which in turn will cause the tumor, or lesion, 70 to be disposed in the proper location for treatment by linear accelerator 40. The computer 110, after having compared the actual locations of the light emitting diodes with the previously determined desired locations of the light emitting diodes from the diagnostic study, can indicate to the user of apparatus 60, either by text or a visual diagram (not shown) appearing on the screen (not shown) of computer 110 or by an audible indication from computer 110, whether or not the patient is positioned properly with respect to treatment table 42 and gantry 41 of linear accelerator 40. Computer 100 can further indicate in which direction, or directions, it is necessary to move the patient 50 so that proper positioning of patient 50 may be achieved.

Once the proper positioning of patient 50 has been confirmed, the desired radiation therapy treatment can begin. If the radiation therapy treatment is a rotational therapy treatment plan, whereby gantry 41 rotates about patient 50, camera 102 can continuously monitor the location of the plurality of light emitting diodes 90, 90', and 90" to determine whether or not proper patient positioning is being maintained. If the patient 50 moves, whereby the location of tumor, or lesion, 70 is changed, computer 110 can indicate to the user that the radiation therapy treatment should be stopped, or computer 110 can automatically terminate the radiation therapy treatment plan. Computer 110 can also be programmed to provide for an acceptable amount of movement of patient 50, whereby if the limit of acceptable movement is exceeded, a visual or audible indication of that fact can be provided to the user. If a rotational radiation therapy treatment plan is being utilized, camera 102 may generate an image of the light emitting diodes 90, 90', and 90", at each time gantry 41 rotates through a predetermined angle. If a static radiation therapy treatment is being delivered by linear accelerator 40, or other radiation therapy device, camera 102 may continuously view and generate a continuous image of the plurality of light emitting diodes, and the locations of the light emitting diodes viewed are continuously compared to the previously determined desired locations of the light emitting diodes.

When apparatus 60, including linear accelerator 40 is utilized to provide radiation therapy treatment to a lesion, or tumor, 70 which is not disposed within the head 51 of patient 50, apparatus 60 may be utilized in the same manner previously described, provided a plurality of light emitting diodes 90 are secured directly to the patient, in the manner previously described, including the step of immobilizing the patient with respect to the treatment table 42.

Figure 3:
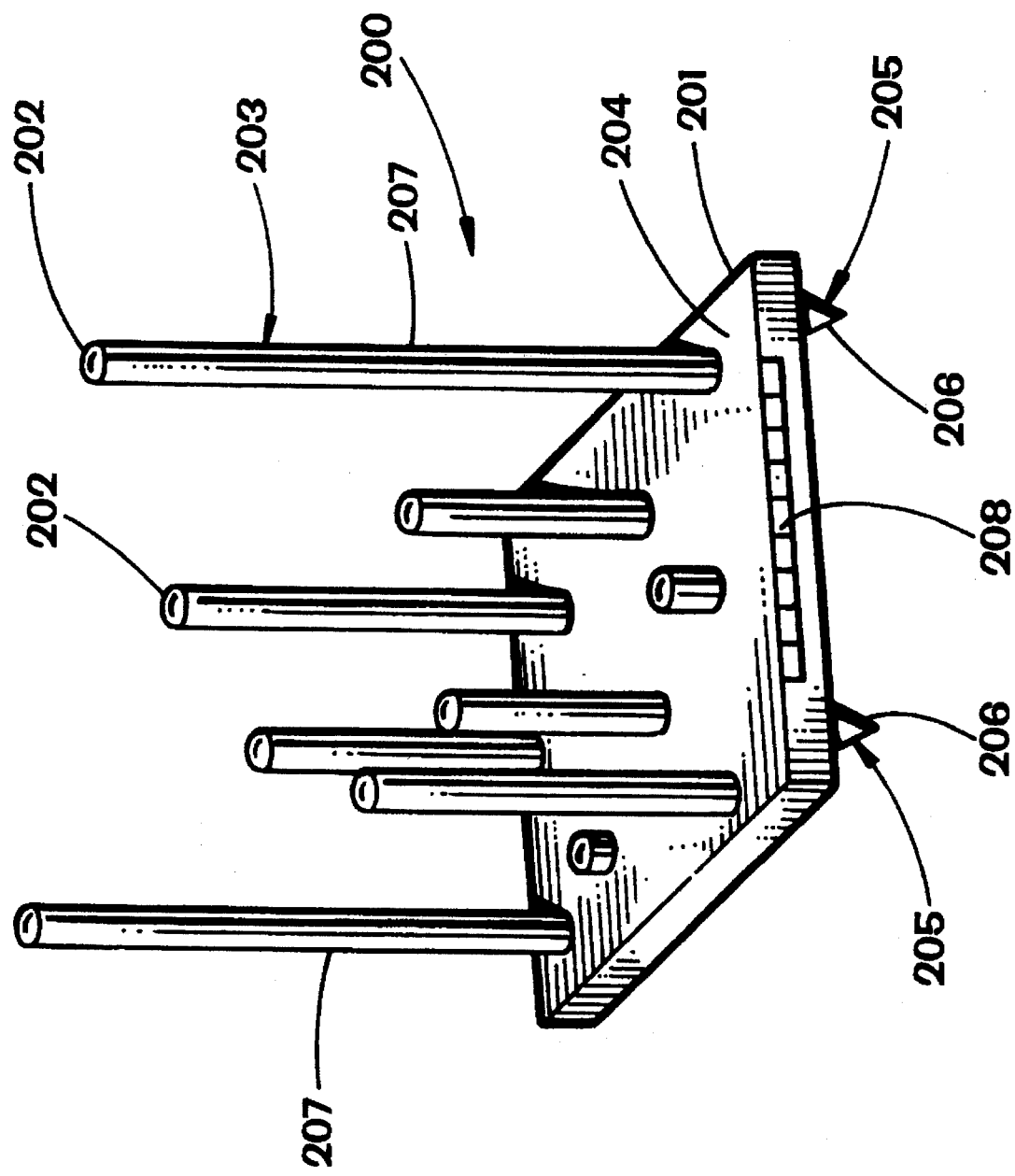
FIG. 3 is a perspective view of a calibration fixture in accordance with the present invention.

Before apparatus 60 is first used in connection with linear accelerator 40, to verify correct positioning of the patient upon treatment table 42, it is necessary to calibrate apparatus 60. A calibration fixture 200 is illustrated in FIG. 3 which has been found to be satisfactory for calibrating apparatus 60. Calibration fixture 200 includes a base member 201, a plurality of light emitting diodes 202 disposed in a known spatial relationship with respect to each other, and a means for supporting 203 each of the plurality of light emitting diodes 202 upon the base member 201. Preferably, base member 201 has an upper planar surface 204 and is provided with means for leveling 205 base member 201. Leveling means may be any conventional leveling device, such as a plurality of leveling feet 206, one leveling foot being disposed in each corner of base member 201. Supporting means 203 may be any suitable structure which has the requisite strength and rigidity to support the plurality of light emitting diodes 202 in the known spatial relationship with respect to each other, such as a plurality of upwardly extending light emitting diode support members 207 which may be formed of a suitable plastic material having a tubular construction. A thin wire (not shown) may extend from each light emitting diode 202 through support member 207 to an electrical contact strip 208 disposed upon base member 201, whereby suitable electric power may be provided to each light emitting diode 202. The plurality of light emitting diodes 202 are preferably disposed in a spaced relationship from the base member 201, whereby each light emitting diode 202 is not coplanar with base member 201, in that each light emitting diode 202 lies in a different plane with respect to the base member, or a different vertical distance from base member 201. Preferably, at least six light emitting diodes 202 are disposed in the known spatial relationship with respect to each other. The known spatial relationship with respect to each other can be determined by accurately measuring the location, or three dimensional coordinates, of each light emitting diode 202 with respect to the base member and with respect to the other light emitting diodes.

Calibration fixture 200 may be used to calibrate apparatus 60 in the following manner. The calibration fixture 200 is placed upon the treatment table 42 of FIGS. 1 and 2 and images are generated by camera 102 from two different predetermined positions with respect to calibration fixture 200, in the same manner as two images were generated by camera 102 of the light emitting diodes 90, 90', and 90", at locations 120, 121 of gantry 41. When the images are generated of calibration fixture 200, the angle between the two positions of gantry 41 used with calibration fixture 200 should be the same angle utilized between the locations 120, 121 of gantry 41 when apparatus 60 is used to properly position patient 50, as previously described in connection with FIGS. 1 and 2. The images of the light emitting diodes 202 are digitized by a conventional frame grabber and processed by computer 110. The optical resolution of a typical camera 102 and frame grabber digitizer results in each light emitting diode being represented by ten to twenty pixels of the image. A histogram analysis is performed on the pixelated images to create an adaptive threshold which is used to determine the centroid of each light emitting diode 202. The ordering of the light emitting diodes 202 is determined by viewing one light emitting 202 at a time under control of computer 110. The images from each camera location 120, 121 (FIG. 2) and the known three dimensional coordinates of light emitting diodes 202 and calibration fixture 200 are then utilized to develop a conventional, standard transformation matrix which defines the relative coordinate system for each camera location or position, 120, 121. The set of two dimensional centroid coordinates from the camera images, and the known three dimensional locations of the light emitting diodes 202 and calibration fixture 200 are utilized to develop the transformation matrix. By the use of a known triangulation algorithm, as previously described, images from two or more distinct camera and gantry positions, such as 120, 121 of FIG. 2, may be utilized to determine the location of any point within the field of view 104 of camera 102. Preferably, calibration data is obtained with calibration fixture 200 for a multitude of angular locations of gantry 41 and camera 120 to insure that the coordinate transformation matrix will be accurate.

It is to be understood that the invention is not to be limited to the exact details of construction, operation, exact materials or embodiments shown and described, as obvious modifications and equivalents will be apparent to one skilled in the art; for example, as previously described, two or more cameras could be secured to the gantry. Accordingly, the invention is therefore to be limited only by the scope of the appended claims.

I claim:

1. Apparatus for treating a patient with radiation therapy treatment of a lesion within the patient's body comprising:

a linear accelerator, including a rotatable gantry, a treatment table, and a means for focusing a beam of radiation;

a means for immobilizing a portion of the patient with respect to the treatment table associated with the treatment table; and a means for positioning the patient upon the treatment table, including:

a plurality of light emitting diodes, including means for mounting the plurality of light emitting diodes with respect to the patient;

at least one camera for viewing the plurality of light emitting diodes; and means for mounting the at least one camera to the gantry of the linear acceleration, whereby as the gantry rotates, the at least one camera rotates with the gantry and views the plurality of light emitting diodes from at least two different angular positions of the gantry with respect to the treatment table.

2. The apparatus of claim 1, wherein the at least one camera is a single camera.

3. The apparatus of claim 1, wherein the at least one camera is a charged coupled device camera.

4. The apparatus of claim 1, wherein the means for mounting the plurality of light emitting diodes includes a means for mounting at least one light emitting diode in an external auditory canal of an ear of the patient.

5. The apparatus of claim 4, wherein the means for mounting at least one light emitting diode in an ear of the patient includes a quantity of rapidly setting material, which is adapted to be disposed within, and conform to, the external auditory canal, and the light emitting diode is inserted into the rapidly setting material.

6. The apparatus of claim 1, wherein the means for mounting the plurality of light emitting diodes includes a means for mounting at least one light emitting diode to the means for immobilizing a portion of the patient.

7. The apparatus of claim 1, wherein the means for mounting the plurality of light emitting diodes includes a means for mounting at least one light emitting diode to the body of the patient.

8. A method for positioning a patient upon a treatment table of a linear accelerator for providing radiation therapy treatment of a lesion within the patient's body, the linear accelerator having a rotatable gantry, comprising the steps of:

providing at least one camera mounted to the gantry of the linear accelerator;

immobilizing a portion of the patient with respect to the treatment table with a means for immobilizing associated with the treatment table;

mounting a plurality of light emitting diodes with respect to the patient;

disposing the gantry, with the at least one camera mounted thereto, in a first predetermined position with respect to the patient and generating a first image of the plurality of light emitting diodes with the at least one camera;

rotating the gantry, with the at least one camera mounted thereto, to a second predetermined position with respect to the patient, and generating a second image of the plurality of light emitting diodes with the at least one camera;

determining, from the first and second images, the location of the light emitting diodes with respect to the treatment table; and comparing the location of the light emitting diodes with respect to the treatment table, to a previously determined desired location of the light emitting diodes with respect to the treatment table, whereby if the location of the light emitting diodes with respect to the treatment table indicates the patient is not properly positioned, the patient may be moved whereby the light emitting diodes will be disposed in the desired position.

9. The method of claim 8, including the step of providing a single camera mounted to the gantry of the linear accelerator.

10. The method of claim 8, including the step of mounting at least one of the light emitting diodes with respect to the patient by mounting at least one light emitting diode to the means for immobilizing the patient.

11. The method of claim 10, including the step of mounting at least three light emitting diodes to the means for immobilizing the patient.

12. The method of claim 11, including the step of disposing the three light emitting diodes in a noncoplanar relationship with respect to a plane disposed perpendicular to a longitudinal axis of the treatment table.

13. The method of claim 8, including the step of mounting at least one of the light emitting diodes with respect to the patient by mounting at least one light emitting diode upon the patient.

14. The method of claim 13, including the step of mounting at least one light emitting diode in an external auditory canal of an ear of the patient.

15. The method of claim 14, wherein the at least one light emitting diode is mounted in an external auditory canal of the patient by disposing a quantity of a rapidly setting material in the external auditory canal and causing the material to conform to the shape of the external auditory canal, and at least one light emitting diode is disposed within the rapidly setting material before the material has completely set.

16. The method of claim 15, including the step of mounting a light emitting diode in each ear of the patient.

17. The method of claim 8, including the step of utilizing at least one camera having an angle sensor associated therewith.

18. The method of claim 8, including the step of utilizing as the at least one camera, a charged coupled device camera.

19. The method of claim 8, including the step of calibrating the at least one camera with respect to the treatment table before immobilizing at least a portion of the patient with respect to the treatment table.

20. The method of claim 19, including the steps of utilizing a calibration fixture to calibrate the at least one camera and providing the calibration fixture with a plurality of light emitting diodes disposed in a known spatial relationship with each other.

21. The method of claim 20, wherein the at least one camera has a field of view, and including the steps of disposing the gantry, with the at least one camera mounted thereto, in a first predetermined position with respect to the calibration fixture generating a first image of the plurality of light emitting diodes with the at least one camera; rotating the gantry, with the at least one camera mounted thereto, to a second predetermined position with respect to the calibration fixture and generating a second image of the plurality of light emitting diodes with the at least one camera; and determining, from the first and second images, the location of any point within the field of view of the at least one camera.

22. The method of claim 8, including the steps of continuously monitoring the location of the plurality of light emitting diodes during the rotation of the gantry while a radiation therapy treatment is provided to the patient.

23. The method of claim 22, including the step of indicating an undesired location of at least one of the plurality of light emitting diodes during the radiation therapy treatment.

24. The method of claim 8, including the steps of continuously monitoring the location of the plurality of light emitting diodes while a static radiation therapy treatment is provided to the patient.

25. The method of claim 24, including the step of indicating an undesired location of at least one of the plurality of light emitting diodes during the radiation therapy treatment.

* * * * *